US010321817B2

(12) United States Patent
Hane et al.

(10) Patent No.: US 10,321,817 B2
(45) Date of Patent: Jun. 18, 2019

(54) IMAGE DISPLAY APPARATUS, METHOD OF PROCESSING, AND PROCESSING APPARATUS

(71) Applicant: TOHOKU UNIVERSITY, Sendai-shi, Miyagi (JP)

(72) Inventors: Kazuhiro Hane, Sendai (JP); Toru Nakazawa, Sendai (JP); Takashi Sasaki, Sendai (JP)

(73) Assignee: TOHOKU UNIVERSITY, Sendai-shi, Miyagi (JP)

( * ) Notice: Subject to any disclaimer, the term of this patent is extended or adjusted under 35 U.S.C. 154(b) by 58 days.

(21) Appl. No.: 15/717,451

(22) Filed: Sep. 27, 2017

(65) Prior Publication Data
US 2018/0014723 A1 Jan. 18, 2018

Related U.S. Application Data

(63) Continuation of application No. PCT/JP2016/057497, filed on Mar. 10, 2016.

(30) Foreign Application Priority Data

Mar. 31, 2015 (JP) .................................. 2015-070696

(51) Int. Cl.
*A61B 3/12* (2006.01)
*A61B 3/00* (2006.01)
(Continued)

(52) U.S. Cl.
CPC ............ *A61B 3/005* (2013.01); *A61B 3/0008* (2013.01); *A61B 3/10* (2013.01); *A61B 3/12* (2013.01);
(Continued)

(58) Field of Classification Search
CPC ..... A61B 3/0008; A61B 3/1233; A61B 3/005; A61B 3/158
(Continued)

(56) References Cited

U.S. PATENT DOCUMENTS 5,298,927 A 3/1994 Konishi et al.
2002/0036750 A1* 3/2002 Eberl ....................... A61B 3/12
351/207

(Continued)

FOREIGN PATENT DOCUMENTS

JP 4-242627 A 8/1992
JP 11-259225 A 9/1999
(Continued)

OTHER PUBLICATIONS

International Search Report issued for corresponding International Patent Application No. PCT/JP2016/057497, dated May 31, 2016.
(Continued)

Primary Examiner — Hung X Dang
(74) Attorney, Agent, or Firm — Myers Wolin, LLC

(57) ABSTRACT

An image display apparatus includes: a light source part generating a plurality of light rays corresponding to respective pixels in an image that changes over time; a projecting part defining an optical path from the light source part to an eye, and forming the image on a retina of the eye by projecting the generated light rays directly on the retina through the optical path; a splitting part splitting a plurality of reflection light rays from positions in a certain site of the eye on the optical path, the positions corresponding to the respective pixels; a detecting part detecting intensities of the reflection light rays that have been split; and a processing part obtaining parameters indicative of conditions of the site at the positions corresponding to the respective pixels, based (Continued)

on intensities of the generated light rays and the intensities of the reflection light rays, for the respective pixels.

10 Claims, 11 Drawing Sheets

(51) Int. Cl.
*A61B 3/10* (2006.01)
*G02B 27/10* (2006.01)
*G03B 21/14* (2006.01)
*G06T 7/00* (2017.01)
*G02B 27/01* (2006.01)

(52) U.S. Cl.
CPC ....... *G02B 27/0172* (2013.01); *G02B 27/106* (2013.01); *G03B 21/14* (2013.01); *G06T 7/0012* (2013.01); *A61B 3/102* (2013.01); *G02B 2027/0178* (2013.01); *G06T 2207/20024* (2013.01); *G06T 2207/30041* (2013.01)

(58) Field of Classification Search
USPC .......................... 351/221, 246, 205
See application file for complete search history.

(56) References Cited

U.S. PATENT DOCUMENTS

| | | |
|---|---|---|
| 2008/0225226 A1 | 9/2008 | Fujishiro et al. |
| 2008/0309881 A1 | 12/2008 | Huang et al. |
| 2009/0219484 A1 | 9/2009 | Ebisawa |
| 2014/0313479 A1 | 10/2014 | Nozato et al. |
| 2015/0009236 A1 | 1/2015 | Saito |
| 2015/0042950 A1 | 2/2015 | Yamazaki |
| 2016/0179193 A1 | 6/2016 | Du et al. |

FOREIGN PATENT DOCUMENTS

| | | |
|---|---|---|
| JP | 2006-15061 A | 1/2006 |
| JP | 2008-228781 A | 10/2008 |
| JP | 2010-529896 A | 9/2010 |
| JP | 2014-209980 A | 11/2014 |
| JP | 2014-222289 A | 11/2014 |
| JP | 2015-15563 A | 1/2015 |
| JP | 2015-33423 A | 2/2015 |
| WO | 2007/113975 A1 | 10/2007 |
| WO | 2015/012280 A1 | 1/2015 |
| WO | 2015/027599 A1 | 3/2015 |

OTHER PUBLICATIONS

Kuriyama et al, "Wearable display with personal authentication", copyright 2014 IEE Japan, Oct. 14, 2014, with English abstract and English translation.

International Preliminary Report on Patentability issued for corresponding International Patent Application No. PCT/JP2015/057497, dated Sep. 30, 2017.

Notification of Reasons for Refusal issued by the Japan Patent Office for corresponding Japanese Patent Application No. 2015-070696, dated Feb. 12, 2019, with an English translation.

* cited by examiner

IMAGE DISPLAY APPARATUS, METHOD OF PROCESSING, AND PROCESSING APPARATUS

CROSS-REFERENCE TO RELATED APPLICATIONS

This application is a continuation application of International Application PCT/JP2016/057497 filed on Mar. 10, 2016, which claims priority to Japanese Patent Application No. 2015-070696, filed on Mar. 31, 2015. The contents of these applications are incorporated herein by reference in their entirety.

TECHNICAL FIELD

The present invention relates to an image display apparatus, a method of processing, and a processing apparatus.

BACKGROUND ART

An image display apparatuses to be mounted on a head of a human is known which forms an image on the retina of an eye by projecting light directly onto the retina (e.g., Patent Documents 1 and 2, and Non-Patent Document 1). For example, such an image display apparatus is referred to as a head mount display (HMD).

There are two projection techniques employed in HMDs are known: the scanning and the non-scanning projections. In the scanning projection, a laser light ray corresponding to a single pixel scans a plurality of positions corresponding to respective pixels in an image, thereby forming that image on the retina. For the scanning, for example, micro electro mechanical systems (MEMS), such as micro mirrors, are used. In the non-scanning projection, an image is formed on the retina by generating a plurality of light rays that correspond to respective pixels in the image and are arranged in a grid on a plane.

Furthermore, detection apparatuses are known which illuminate light on the retina of an eye of a subject and detect the intensity of light reflecting off the retina (e.g., Patent Documents 3 and 4, and Non-Patent Document 1).

For example, the HMD disclosed in Non-Patent Document 1 forms an image on the retina by means of the scanning projection. Furthermore, the HMD detects the intensity of reflection light from the retina.

Patent Document 1: Japanese Laid-open Patent Publication No. 2015-15563
Patent Document 2: Japanese Laid-open Patent Publication No. 2014-222289
Patent Document 3: Japanese Laid-open Patent Publication No. 2014-209980
Patent Document 4: Japanese Laid-open Patent Publication No. 2015-33423
Non-Patent Document 1: Kuriyama and two others, "Wearable display with personal authentication", *Proceedings of The 31st Sensor Symposium on Sensors, Micromachines and Applied Systems,* IEEJ Sensors and Micromachines Society[Ed], Institute of Electrical Engineers of Japan, Oct. 20, 2014, 21pm3-PS68

SUMMARY OF THE INVENTION

In an examination with a detection apparatus, a subject may feel that performing the examination of their eyes independently from other tasks is annoying. Therefore, it is thought that an examination of eyes is performed while the subject is watching a video.

In the meantime, a plurality of light rays corresponding to respective pixels in an image may have different intensities. Further, the intensity of light reflecting off the retina is strongly correlates to the intensity of the light used to illuminate the retina. Therefore, the intensities of light rays reflecting off the retina when an eye is illuminated with a plurality of light rays corresponding to respective pixels in the image on the retina may not properly indicate the condition of the retina.

One object of the present invention is to provide an image display apparatus with which the condition of an eye of a user can be examined quite precisely without the user being aware that the eye is being examined.

In one aspect, an image display apparatus includes:
a light source part that generates a plurality of light rays corresponding to respective pixels in an image that changes over time;
a projecting part that defines an optical path from the light source part to an eye, and forms the image on a retina of the eye by projecting the plurality of generated light rays directly on the retina through the optical path;
a splitting part that splits a plurality of reflection light rays from positions in a certain site of the eye on the optical path, the positions corresponding to the respective pixels;
a detecting part that detects intensities of the plurality of reflection light rays that have been split; and
a processing part that obtains parameters indicative of conditions of the site at the positions corresponding to the respective pixels, based on intensities of the generated light rays and the intensities of the plurality of reflection light rays, for the respective pixels.

In another aspect, a method of processing includes:
generating a plurality of light rays corresponding to respective pixels in an image that changes over time, by a light source part;
forming the image on a retina of an eye by projecting the plurality of generated light rays directly on the retina through an optical path from the light source part to the eye;
splitting a plurality of reflection light rays from positions in a certain site of the eye on the optical path, the positions corresponding to the respective pixels;
detecting intensities of the plurality of reflection light rays that have been split; and
obtaining parameters indicative of conditions of the site at the positions corresponding to the respective pixels, based on intensities of the generated light rays and the intensities of the plurality of reflection light rays, for the respective pixels.

In another aspect, a processing apparatus adapted to
obtain parameters indicative of conditions of a site at positions corresponding to respective pixels in an image that changes over time, based on intensities of a plurality of light rays generated by an image display apparatus and intensities of a plurality of reflection light rays detected by the image display apparatus, for the respective pixels,
the image display apparatus comprising:
a light source part that generates the plurality of light rays corresponding to the respective pixels;
a projecting part that defines an optical path from the light source part to an eye, and forms the image on a retina of the eye by projecting the plurality of generated light rays directly on the retina through the optical path;

a splitting part that splits the plurality of reflection light rays from positions in the certain site of the eye on the optical path, the positions corresponding to the respective pixels; and a detecting part that detects the intensities of the plurality of reflection light rays that have been split.

The condition of an eye of a user can be examined quite precisely without the user being aware that the eye is being examined.

DETAILED DESCRIPTION OF THE INVENTION

Embodiments of an image display apparatus, a method of processing, a method of detecting, and a processing apparatus of the present invention will be described with reference to FIGS. 1-11.

First Embodiment (Configuration)

Figure 1:
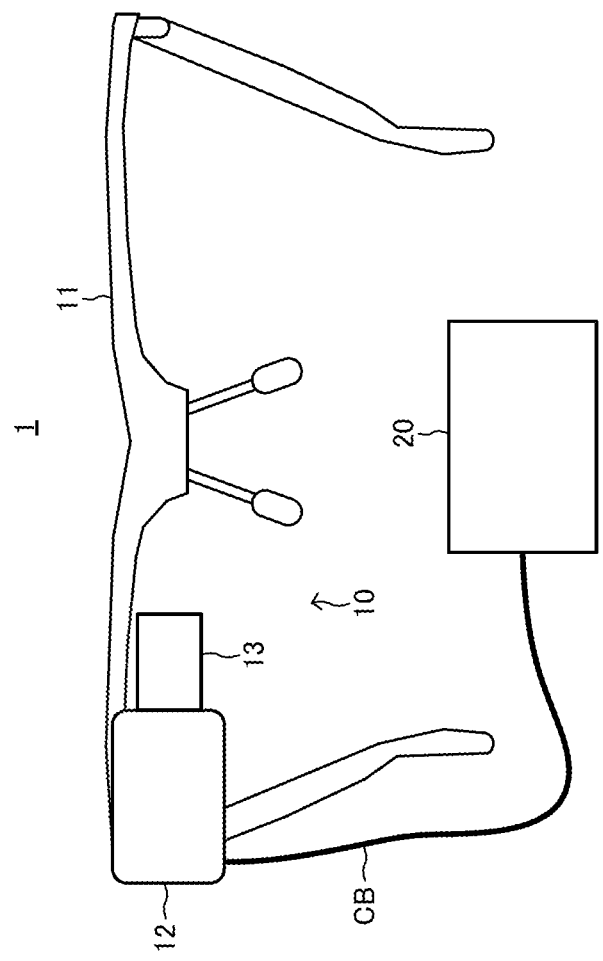
FIG. 1 is a diagram illustrating a configuration of an image display apparatus of a first embodiment.

As depicted in FIG. 1, an image display apparatus 1 of a first embodiment is a glasses-type head mount display (HMD). The image display apparatus 1 may be an HMD other than glasses-type HMDs, such as a cap-type HMD. The type of projection used for the image display apparatus 1 is the non-scanning projection.

The image display apparatus 1 includes a main body 10 and a controller 20. The main body 10 and the controller 20 are connected through a cable CB. The controller 20 includes a battery (not illustrated), and is powered by the battery and feeds the power from the battery to the main body 10. The main body 10 is powered by the controller 20.

The controller 20 communicates with the main body 10 through the cable CB. The controller 20 sends image information indicating an image to the main body 10. In this example, the image information contains light intensities of respective pixels in an image. The main body 10 receives image information from the controller 20, and displays an image indicated in the image information. In this example, the image indicated in the image information changes over time. In other words, the main body 10 displays images or videos in this example.

The main body 10 may include a battery and may be powered by the battery. Alternatively, the main body 10 may be powered through a contactless power transmission or wireless power transmission system. Further, the main body 10 may wirelessly communicate with the controller 20. In this case, the image display apparatus 1 may not include the cable CB.

The main body 10 includes a frame 11, a light source unit 12, and a projecting unit 13. The light source unit 12 is supported by the frame 11. The projecting unit 13 is connected to the light source unit 12. The projecting unit 13 is configured such that the projecting unit 13 is positioned in front of eyes of a user who wears the main body 10. The light source unit 12 and the projecting unit 13 may be embodied with optical integrated circuits. The user may also referred to as a subject.

Figure 2:
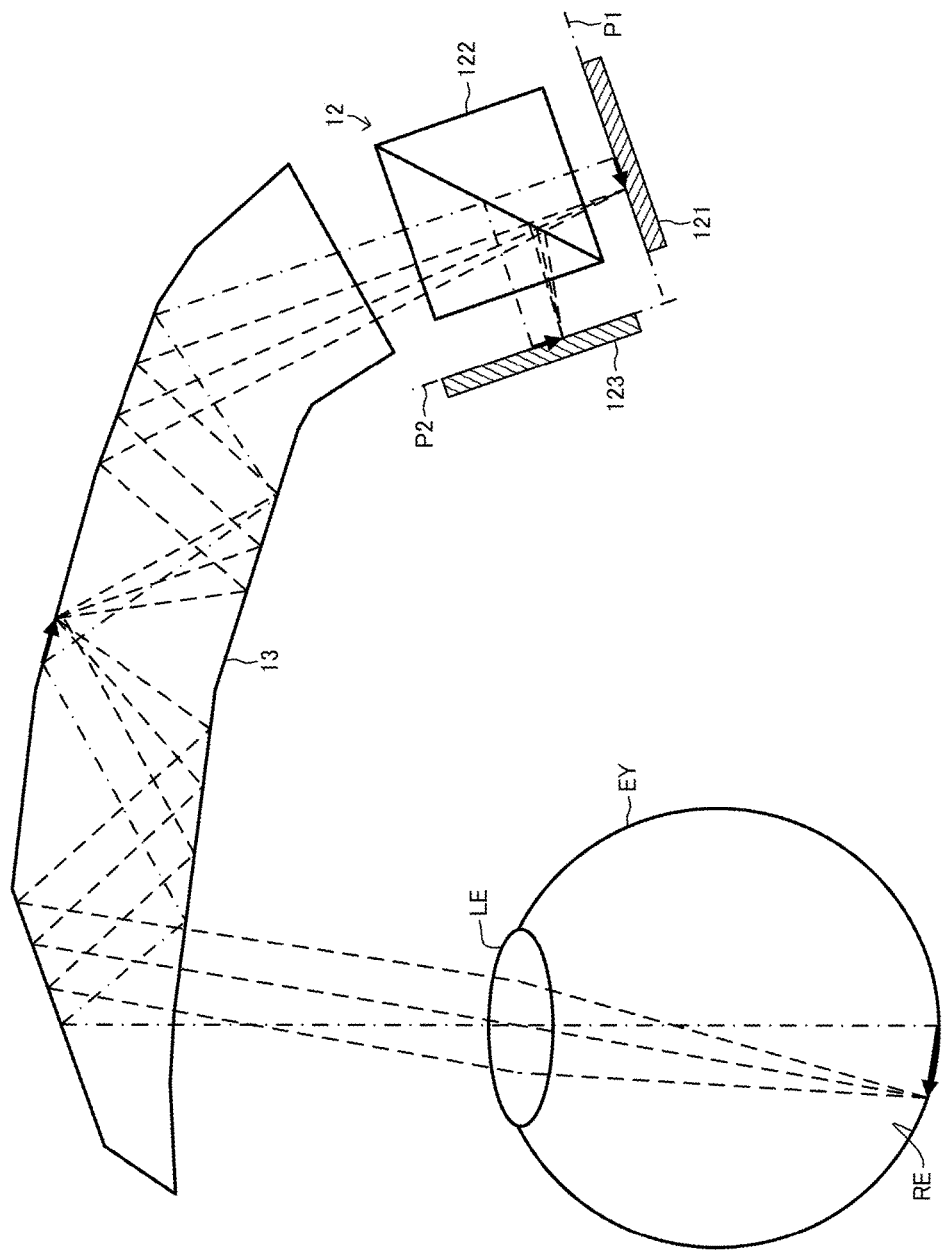
FIG. 2 is a diagram illustrating a configuration of a light source unit and a projecting unit in FIG. 1.

As depicted in FIG. 2, the light source unit 12 includes a light source part 121, a splitting part 122, and a detecting part 123.

The light source part 121 includes a plurality of light sources that are arranged in a grid on a first plane P1. The plurality of light sources generate respective light rays corresponding to the pixels in the image indicated in the image information received from the controller 20.

In this example, each of the light sources generates light rays in N colors. N represents the number of colors generated by each of the light sources. In this example, N is three. In this example, each of the light sources generates light rays in red, blue, and green, respectively. N may be an integer of 1, 2, or 4 or greater. In other words, the light rays generated by each of the light sources include light rays in N colors.

In this example, light rays corresponding to the respective pixels have light intensities of the pixels in the image information.

In this example, the light source part 121 is a liquid crystal display (LCD). The light source part 121 may be a light emitting diode (LED) display, or may be a display other than LCDs, such as an LED liquid crystal display.

The plurality of light rays generated by the light source part 121 enter the splitting part 122. The splitting part 122 guides the plurality of light rays from the light source part 121 toward the projecting unit 13.

The projecting unit 13 defines optical paths from the light source part 121 to an eye EY. The plurality of light rays generated by the light source part 121 enter the projecting unit 13 through the splitting part 122. In this example, a light ray traveling from the light source part 121 toward the eye EY is referred to as a projection light ray. The projecting unit 13 forms an image on a retina RE of the eye EY by projecting the plurality of incoming projection light rays directly to the retina RE through the defined optical paths.

Furthermore, the plurality of light rays reflected at the positions, which are in a certain site of the eye EY, corresponding to the respective pixels in the image to be formed on the retina RE enter the projecting unit 13. In this example, a light ray traveling from the eye EY toward the detecting part 123 is referred to as a reflection light ray. In this example, the certain site of the eye EY is the retina RE of the eye EY.

The projecting unit 13 is one example of a projecting part.

The projection light rays generated by the light sources are reflected at the positions corresponding to the light sources at the retina RE, respectively. The reflected light rays (in other words, reflection light rays) travel on the optical paths from the retina RE toward the respective light sources, which are the same as the optical paths on which the light rays have traveled to reach the retina RE from the respective light sources. In other words, the reflection light rays travel on the same optical paths as those of the projection light rays from which the reflection light rays are originated, but in the direction opposite to the direction of the projection light rays.

The plurality of reflection light rays from the projecting unit 13 enter the splitting part 122. The splitting part 122 splits the plurality of reflection light rays incoming from the projecting unit 13, and guides the plurality of split reflection light rays to the detecting part 123. In this example, the splitting part 122 is a beam splitter.

The detecting part 123 includes a plurality of detectors that are arranged in a grid on a second plane P2. The plurality of detectors detect the respective reflection light rays that have been split by the splitting part 122. In this example, the plurality of detectors detect the intensities of the respective reflection light rays that have been split by the splitting part 122.

In this example, the detecting part 123 is a solid state image sensor. The solid state image sensor is a charge-coupled device (CCD) image sensor, or a complementary metal oxide semiconductor (CMOS) image sensor, for example.

Figure 3:
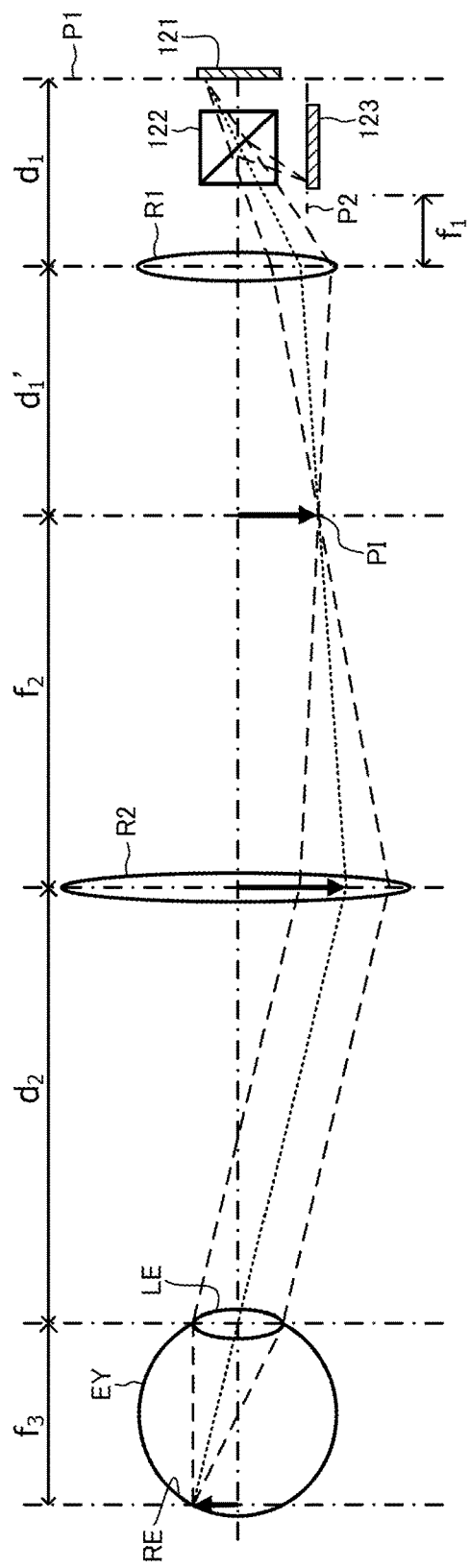
FIG. 3 is a conceptual illustration depicting an optical system employed by the light source unit and the projecting unit in FIG. 1.

The optical system employed by the light source unit 12 and the projecting unit 13 will be described. FIG. 3 is a conceptual representation of the optical system employed by the light source unit 12 and the projecting unit 13. In this example, the projecting unit 13 functions similarly to a first lens R1 and a second lens R2.

The first lens R1 is disposed at the position where the distance $d_1$ between the first plane P1 of the light source part 121 and the principal plane of the first lens R1 becomes longer than the focal length $f_1$ of the first lens R1. The first lens R1 focuses the image formed on the first plane P1 by the light source part 121, on the plane where the distance from the principal plane of the first lens R1 equals the distance $d_1'$. The plane where the distance from the principal plane of the first lens R1 equals the distance $d_1'$ may also be referred to as the primary image surface (or first image surface) PI.

The focal length $f_1$ of the first lens R1, the distance $d_1$ between the first plane P1 and the principal plane of the first lens R1, and the distance $d_1'$ between the principal plane of the first lens R1 and the primary image surface PI satisfy the relationship represented by the following Formula 1:

$$\frac{1}{f_1} = \frac{1}{d_1} + \frac{1}{d_1'} \qquad \text{Formula 1}$$

The second lens R2 is disposed at the position where the distance between the primary image surface PI and the principal plane of the second lens R2 coincides with the focal length $f_2$ of the second lens R2. The second lens R2 guides a light ray at a point on the primary image surface PI, as light rays traveling in parallel to each other (in other words, parallel light rays). In this example, the distance $d_2$ between the principal plane of the second lens R2 and the principal plane of the lens LE of the eye EY is longer than the focal length $f_2$ of the second lens R2.

The lens LE of the eye EY is adjusted such that the focal length $f_3$ of the lens LE coincides with the distance between the principal plane of the lens LE and the retina RE. The lens LE is a part (e.g., cornea, pupil, crystalline lens, and the like) of the eye EY having a function to refract light rays.

As a result, the lens LE of the eye EY converges parallel light rays incoming from the second lens R2 on a single point in the retina RE. This means that the lens LE of the eye EY focuses the image formed on the primary image surface PI, on the retina RE.

As set forth above, the light rays generated by the light sources are reflected at the positions corresponding to the light sources in the retina RE, respectively. The reflection light rays travel on the optical paths from the retina RE toward the respective light sources, which are the same as the optical paths on which the light rays have traveled to reach the retina RE from the respective light sources.

The splitting part 122 splits the reflection light rays on the optical paths between the first lens R1 and the light source part 121. The split reflection light rays for the respective pixels in the image enter the detectors in the detecting part 123.

In other words, for each of the pixels in the image, any of two of the position of the light source on the first plane P1, the location where the light ray converges on the retina RE, and the position of detector on the second plane P2 are optically conjugate to each other.

In the meantime, the reflectivity of the retina RE is quite low. Nevertheless, in accordance with the image display apparatus 1, reflection light rays can be collected to detectors with a high efficiency.

The location of the light source part 121 and the location of the detecting part 123 may be interchangeable.

Figure 4:
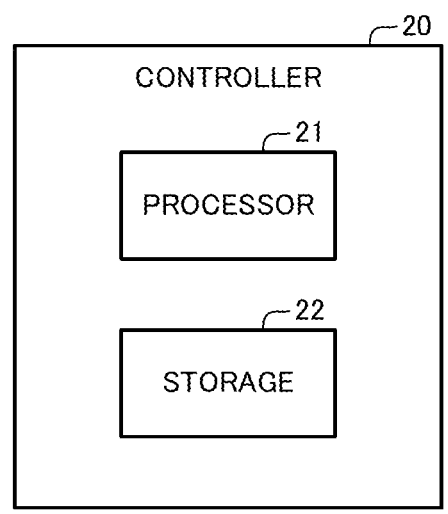
FIG. 4 is a block diagram illustrating a configuration of a controller in FIG. 1.

As depicted in FIG. 4, the controller 20 includes a processor 21 and a storage 22.

The processor 21 embodies later-described functions by executing a program stored in the storage 22. In this example, the processor 21 is a central processing unit (CPU). The processor 21 may be embodied by a digital signal processor (DSP) or a programmable logic device (PLD).

The storage 22 stores information in a readable and writable manner. The storage 22 includes at least one of a random access memory (RAM), a read only memory (ROM), a hard disk drive (HDD), a solid state disk (SSD), a semiconductor memory, and an organic memory, for example. The storage 22 may include a recording medium, such as a flexible disk, an optical disk, a magneto-optical disk, and a semiconductor memory, and a reader that can read information from the recording medium.

The controller 20 may be embodied by an integrated circuit, such as a large scale integration (LSI), for example.

Figure 5:
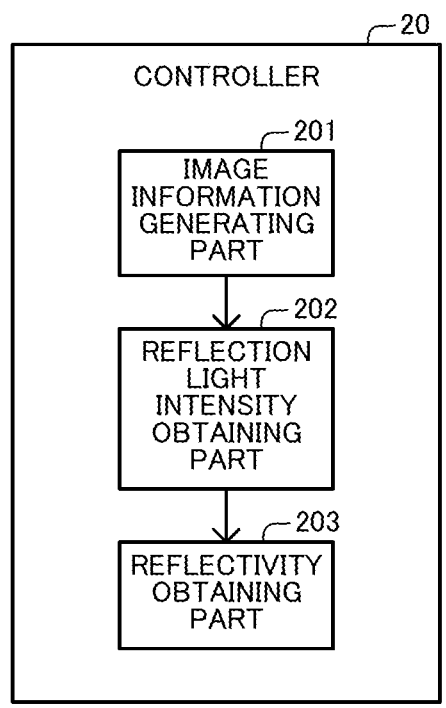
FIG. 5 is a block diagram illustrating functions of the controller in FIG. 1.

As depicted in FIG. 5, the controller 20 includes functions of an image information generating part 201, a reflection light intensity obtaining part 202, and a reflectivity obtaining part 203. The reflectivity obtaining part 203 is one example of a processing part.

The image information generating part 201 generates image information including the light intensities for the respective pixels in the image. In this example, the light intensities of the pixels are represented by Formula 2:

$$\begin{pmatrix} I_n(0,0) & I_n(0,1) & \cdots & I_n(0,j_0) \\ I_n(1,0) & I_n(1,1) & \cdots & I_n(1,j_0) \\ \vdots & \vdots & \ddots & \vdots \\ I_n(i_0,0) & I_n(i_0,1) & \cdots & I_n(i_0,j_0) \end{pmatrix} \qquad \text{Formula 2}$$

where $I_n(i, j)$ represents the intensity of the light ray of the pixel of the $i^{th}$ row and $j^{th}$ column in $n^{th}$ color, among the light ray colors generated by the light source part 121; n represents an integer from 1 to N; i represents an integer from 0 to $i_0$, j represents an integer from 0 to $j_0$; $i_0$ represents the value obtained by subtracting one from the pixel count in the X axis direction; and $j_0$ represents the value obtained by subtracting one from the pixel count in the Y axis direction orthogonal to the X axis direction.

The light source part 121 generates, for each of the pixels in the image indicated in the image information generated by the image information generating part 201, a light ray having a light intensity for that pixel in the image information.

The reflection light intensity obtaining part 202 obtains, for each of the colors of the light rays generated by the light source part 121, the intensities of the light rays corresponding to the respective pixels, which are detected by the detecting part 123, as reflection light intensities. The reflection light intensity obtaining part 202 obtains the intensities of the light rays detected by the detecting part 123, by receiving them from the main body 10.

In the meantime, the intensity of a reflection light ray $I_{rn}(i, j)$ in the $n^{th}$ color for the pixel of the $i^{th}$ row and $j^{th}$ column is represented by Formula 3:

$$I_{rn}(i,j) = \alpha R_n(i,j) I_n(i,j) \qquad \text{Formula 3}$$

where $R_n(i, j)$ represents the reflectivity of the retina RE of the $n^{th}$ color at the position corresponding to the pixel of the $i^{th}$ row and $j^{th}$ column; and α represents the detection efficiency of a reflection light ray. The detection efficiency decreases as the light intensity attenuates on the optical path from the retina RE to the detector.

From Formula 3, Formula 4 is derived, which represents the product of the reflectivity $R_n(i, j)$ in the $n^{th}$ color for the pixel of the $i^{th}$ row and $j^{th}$ column and the detection efficiency α:

$$\alpha R_n(i,j) = \frac{I_{rn}(i,j)}{I_n(i,j)} \qquad \text{Formula 4}$$

Thus, the reflectivity obtaining part 203 obtains parameters indicative of the conditions of the retina RE, based on the intensities of light rays $I_n(i, j)$ indicated in the image information generated by the image information generating part 201, the intensities of reflection light rays $I_{rn}(i, j)$ obtained by the reflection light intensity obtaining part 202, and Formula 4. In this example, the parameter indicative of the condition of the retina RE is the product of the reflectivity $R_n(i, j)$ and the detection efficiency α.

The parameter indicative of the condition of the retina RE may be the reflectivity $R_n(i, j)$. In this case, the reflectivity obtaining part 203 may use a value that is determined empirically in advance, as the detection efficiency α. Alternatively, the reflectivity obtaining part 203 may estimate the detection efficiency α in accordance with a predetermined algorithm.

The reflectivity obtaining part 203 may also obtain a differential value of the parameter indicative of the condition of the retina RE, with respect to the variable i representing the X-axis direction position in the image. The reflectivity obtaining part 203 may also obtain a differential value of the parameter indicative of the condition of the retina RE, with respect to the variable j representing the Y-axis direction position in the image.

The differential value of the parameter indicative of the condition of the retina RE with respect to the position does not contain components of the parameter which are constant for the position. Hence, the differential value of the parameter with respect to the position reflects a change of the reflection light intensity with respect to the position quite precisely. Accordingly, in accordance with the reflectivity obtaining part 203, the condition of the eye EY can be examined quite precisely.

The reflectivity obtaining part 203 may obtain the parameters indicative of the conditions of the retina RE, based on the ambient light intensity. The ambient light may also be referred to as the environment light. When the ambient light is taken into consideration, the intensity of the reflection light ray $I_{rn}(i, j)$ in the $n^{th}$ color for the pixel of the $i^{th}$ row and $j^{th}$ column can be represented in Formula 5:

$$I_{rn}(i,j) = \alpha R_n(i,j) I_n(i,j) + I_0 \qquad \text{Formula 5}$$

where $I_0$ represents the ambient light intensity. From Formula 5, Formula 6 is derived, which represents the product of the reflectivity $R_n(i, j)$ in the $n^{th}$ color for the pixel of the $i^{th}$ row and $j^{th}$ column and the detection efficiency α:

$$\alpha R_n(i,j) = \frac{I_{rn}(i,j) - I_0}{I_n(i,j)} \qquad \text{Formula 6}$$

In such a case, the detecting part 123 detects the ambient light intensity $I_0$, while the light source part 121 generates no light ray.

In accordance with the above configuration, the ambient light intensity can be detected, without requiring a separate detector for detecting it. The ambient light intensity can be detected quite precisely.

For example, the controller 20 obtains the intensities of light rays detected by the detecting part 123 as the ambient light intensity in a predetermined time duration, prior to starting transmission of the image information generated by the image information generating part 201 to the main body 10. The controller 20 may obtain the average of the intensities of light rays detected by the plurality of detectors, as the ambient light intensity.

The controller 20 may also stop transmission of the image information to the main body 10 for a predetermined time period at a predetermined cycle, and may obtain the intensities of the light rays detected by the detecting part 123, as the ambient light intensity, while the transmission of the image information is stopped.

The reflectivity obtaining part 203 may obtain the parameters indicative of the conditions of the retina RE, based on the intensities of light rays $I_n(i, j)$ indicated in the image information generated by the image information generating part 201, the intensities of reflection light rays $I_{rn}(i, j)$ obtained by the reflection light intensity obtaining part 202, the ambient light intensity $I_0$ that is obtained, and Formula 6. The value obtained by subtracting the ambient light intensity $I_0$ from the intensity of the reflection light ray $I_{rn}(i, j)$ is one example of the intensity based on the intensity of the detected reflection light ray.

The reflectivity of a light ray by the retina RE is about 4%, for example. Thus, in the detectors for detecting the intensities of reflection light rays from the retina RE, the ambient light intensity tends to be greater than the intensities of the reflection light rays from the retina RE. Hence, a high precision for detections of the intensities of reflection light rays from the retina RE may not be achieved unless the intensities of light rays illuminating the retina RE is sufficiently high relative to the ambient light intensity.

However, as the intensities of light rays illuminating the retina RE is increased, the user of the image display apparatus 1 becomes more annoyed by the glare. In contrast, in accordance with the above-described configuration, the effect of the ambient light intensity on the parameter indicative of the condition of the retina RE can be suppressed. As a result, the condition of the eye EY can be examined quite precisely.

Integrating both of the sides of Formula 3 for the time duration from 0 to T gives Formula 7. As represented by Formulae 8 and 9, defining the integral value C(i, j) of the light intensity $I_n(i, j)$ indicated in the image information over the above time duration, and the integral value D(i, j) of the intensity of the reflection light ray $I_m(i, j)$ over the above time duration, Formula 7 gives Formula 10. From Formula 10, Formula 11 is derived, which represents the product of the reflectivity $R_n(i, j)$ in the $n^{th}$ color for the pixel of the $i^{th}$ row and $j^{th}$ column and the detection efficiency α:

$$\int_0^T I_m(i, j)dt = \alpha R_n(i, j) \int_0^T I_n(i, j)dt \quad \text{Formula 7}$$

$$C(i, j) = \int_0^T I_n(i, j)dt \quad \text{Formula 8}$$

$$D(i, j) = \int_0^T I_m(i, j)dt \quad \text{Formula 9}$$

$$D(i, j) = \alpha R_n(i, j)C(i, j) \quad \text{Formula 10}$$

$$\alpha R_n(i, j) = \frac{D(i, j)}{C(i, j)} \quad \text{Formula 11}$$

In the meantime, the intensities of the detected reflection light rays may contain an error component that deviates over time. The error component is induced by a change in the states of the eye EY (e.g., eye movements, dilation or contraction of the pupil, a blink of the eye, or the like), for example.

Therefore, the reflectivity obtaining part 203 may obtain the value obtained by dividing the integral value D(i, j) of the intensity of the reflection light ray $I_m(i, j)$ over the above time duration, by the integral value C(i, j) of the light intensity $I_n(i, j)$ indicated in the image information over the above time duration, as the parameter indicative of the condition of the retina RE, as represented by Formula 11.

In accordance with the above configuration, the effect of the above-described error component on the parameter indicative of the condition of the retina RE can be suppressed. As a result, the condition of the eye EY can be examined quite precisely without the user being aware that their eye EY is being examined.

Furthermore, integrating both of the sides of Formula 5 for the time duration from 0 to T gives Formula 12. Based on Formulae 8 and 9, Formula 13 is derived from Formula 12. From Formula 13, Formula 14 is derived, which represents the product of the reflectivity $R_n(i, j)$ in the $n^{th}$ color for the pixel of the $i^{th}$ row and $j^{th}$ column and the detection efficiency α:

$$\int_0^T I_m(i, j)dt = \alpha R_n(i, j) \int_0^T I_n(i, j)dt + I_0 T \quad \text{Formula 12}$$

$$D(i, j) = \alpha R_n(i, j)C(i, j) + I_0 T \quad \text{Formula 13}$$

$$\alpha R_n(i, j) = \frac{D(i, j) - I_0 T}{C(i, j)} \quad \text{Formula 14}$$

The reflectivity obtaining part 203 may obtain, as the parameter indicative of the condition of the retina RE, the value obtained by dividing the value obtained by subtracting the product of the ambient light intensity $I_0$ and the length T of the above-described time duration from the integral value D(i, j) of the intensity of the reflection light ray $I_m(i, j)$ over the above-described time duration, by the integral value C(i, j) of the light intensity $I_n(i, j)$ indicated in the image information over the above-described time duration as represented by Formula 14.

In accordance with the above configuration, the effect of the above-described error component on the parameter indicative of the condition of the retina RE can be suppressed. As a result, the condition of the eye EY can be examined quite precisely without the user being aware that their eye EY is being examined.

Further, differentiating both of the sides of Formula 13 with respect to the variable i representing the X-axis direction position in the image gives Formula 15:

$$\frac{dD(i, j)}{di} = \alpha \frac{dR_n(i, j)}{di}C(i, j) + \alpha R_n(i, j)\frac{dC(i, j)}{di} \quad \text{Formula 15}$$

The reflectivity obtaining part 203 may obtain the parameter indicative of the condition of the retina RE, based on the integral value C(i, j), the differential value of the integral value C(i, j) with respect to the variable i, the differential value of the integral value D(i, j) with respect to the variable i, and Formula 15.

Further, differentiating both of the sides of Formula 13 with respect to the variable j representing the Y-axis direction position in the image gives Formula 16:

$$\frac{dD(i, j)}{dj} = \alpha \frac{dR_n(i, j)}{dj}C(i, j) + \alpha R_n(i, j)\frac{dC(i, j)}{dj} \quad \text{Formula 16}$$

The reflectivity obtaining part 203 may obtain the parameter indicative of the condition of the retina RE, based on the integral value C(i, j), the differential value of the integral value C(i, j) with respect to the variable j, the differential value of the integral value D(i, j) with respect to the variable j, and Formula 16.

The reflectivity obtaining part 203 may use the reflectivity R (i, j) for the entire light rays generated by the light source part 121 in N colors, or the product of the reflectivity R(i, j) and the detection efficiency α, as the parameter indicative of the condition of the retina RE. In this case, the reflectivity obtaining part 203 may calculate the reflectivity R(i, j) based on Formula 17:

$$R(i, j) = \frac{1}{N}\sum_{n=1}^{N} R_n(i, j) \qquad \text{Formula 17}$$

(Operations)

Next, operations of the image display apparatus 1 will be described.

The controller 20 generates image information, and sends the generated image information to the main body 10.

The main body 10, on the other hand, receives the image information from the controller 20.

The light source part 121 in the main body 10 generates, for each of the pixels in the image indicated in the received image information, a projection light ray having an intensity of light ray for that pixel in the image information.

The projecting unit 13 in the main body 10 directly projects the plurality of projection light rays generated by the light source part 121, on the retina RE of the eye EY. As a result, the image indicated in the image information is formed on the retina RE.

The projection light rays generated by the respective light sources are reflected at the positions corresponding to the respective light sources in the retina RE. The reflection light rays travel on the optical paths from the retina RE toward the respective light sources, which are the same as the optical paths on which the light rays have traveled to reach the retina RE from the respective light sources.

The splitting part 122 in the main body 10 splits the plurality of reflection light rays incoming from the projecting unit 13, and directs the plurality of split reflection light rays to the detecting part 123. The detecting part 123 in the main body 10 detects the intensities of the plurality of reflection light rays that have been split by the splitting part 122.

The controller 20 receives, for each of the colors of the light rays generated by the light source part 121, the intensities of the light rays corresponding to the respective pixels, which are detected by the detecting part 123, from the main body 10, and obtains the received intensities of the light rays as reflection light intensities. The controller 20 obtains the parameters indicative of the conditions of the retina RE, based on the light intensities $I_n(i, j)$ indicated in the generated image information, the obtained intensities of reflection light rays $I_{rn}(i, j)$, and Formula 4.

As set forth above, the image display apparatus 1 of the first embodiment generates a plurality of light rays corresponding to respective pixels in the image by the light source part 121. The image display apparatus 1 further forms the image on the retina RE, by projecting the plurality of generated light rays directly on the retina RE of the eye EY through the optical paths from the light source part 121 to the eye EY.

Additionally, the image display apparatus 1 splits the plurality of reflection light rays from the position corresponding to the plurality of pixels in a certain site of the eye EY on the optical paths. The image display apparatus 1 further detects the intensities of the plurality of reflection light rays that have been split. Additionally, the image display apparatus 1 obtains parameters indicative of conditions at the positions corresponding to the respective pixels in the site of the eye EY, based on the intensities of the generated light rays and the intensities of the detected reflection light rays for the respective pixels.

In accordance with the above configuration, while the user of the image display apparatus 1 watches the image, the parameters are obtained, which reflect the intensities of a plurality of projection light rays corresponding to the respective pixels in the image. As a result, the condition of the retina RE can be examined quite precisely without the user being aware that their eye EY is being examined. In this example, the parameter represents the reflectivity of light.

Furthermore, the light source part 121 in the image display apparatus 1 includes a plurality of light sources arranged in a grid on the first plane P1, which generate a plurality of light rays corresponding to the respective pixels in the image. Additionally, the detecting part 123 in the image display apparatus 1 includes a plurality of detectors arranged in a grid on the second plane P2, which detect the plurality of reflection light rays that have been split.

In accordance with the above configuration, it is possible to reduce the cost for manufacturing the image display apparatus 1, as compared to the configuration where the scanning projection is used and reflection light intensities are detected with a confocal optical system.

Further, as compared to the configuration where the scanning projection is used and reflection light intensities are detected with a confocal optical system, the flexibility of selection of the location to provide the splitting part 122 can be increased. This, in turn, increases the flexibility of setting sites of the eye EY where reflection light intensities are to be detected.

Glaucoma becomes more likely to develop with age. Most of patients do not notice early glaucoma. This tends to delay initiating treatment for glaucoma. The condition of the eyeground including the retina RE strongly correlates to glaucoma. It is expected that onset of glaucoma can be detected in an early stage, based on the parameter indicative of the condition of the retina RE obtained by the image display apparatus 1.

Arteries can be directly observed in the eyeground including the retina RE. It is possible to obtain information indicative of a health condition, such as the progress of arteriosclerosis, from the blood flow rates and waveforms of pulses of the arteries in the eyeground. Such information indicative of a health condition, such as the progress of arteriosclerosis can be obtained, based on the parameter indicative of the condition of the retina RE obtained by the image display apparatus 1.

In the meantime, it is known that a red-eye effect occurs when a photograph is taken at night. The red-eye effect is caused by light reflected by blood, included in reflection light from the eye EY. If such light reflected by blood can be separated, the separated light can be used to determine the blood glucose level. Therefore, it is regarded that the blood glucose level can be determined, based on the parameter indicative of the condition of the retina RE obtained by the image display apparatus 1.

In the meantime, in this example, light rays generated by the light source part 121 are polarized. For this reason, the image display apparatus 1 may include an optical isolator for improving the efficiency of utilization of light. For example, such an optical isolator includes a polarized light beam splitter, a wave plate, and a Faraday element. The image display apparatus 1 may include a transmission-type screen (e.g., micro lens array) that is disposed on the primary image surface PI to control the light distribution.

The light source unit 12 and the projecting unit 13 may be united into a single unit. Alternatively, the light source unit 12 and the projecting unit 13 may be constituted by three or more units.

First Modification to First Embodiment

An image display apparatus of a first modification to the first embodiment will be described. The image display apparatus of the first modification to the first embodiment is different from the image display apparatus of the first embodiment in that reflection light intensity is detected on the surface of the pupil and the iris. Hereinafter, the image display apparatus of the first modification to the first embodiment will be described, focusing on the differences from the first embodiment. In the descriptions of the first modification to the first embodiment, reference symbols that are the same as or corresponding to those of the first embodiment will be used.

Figure 6:
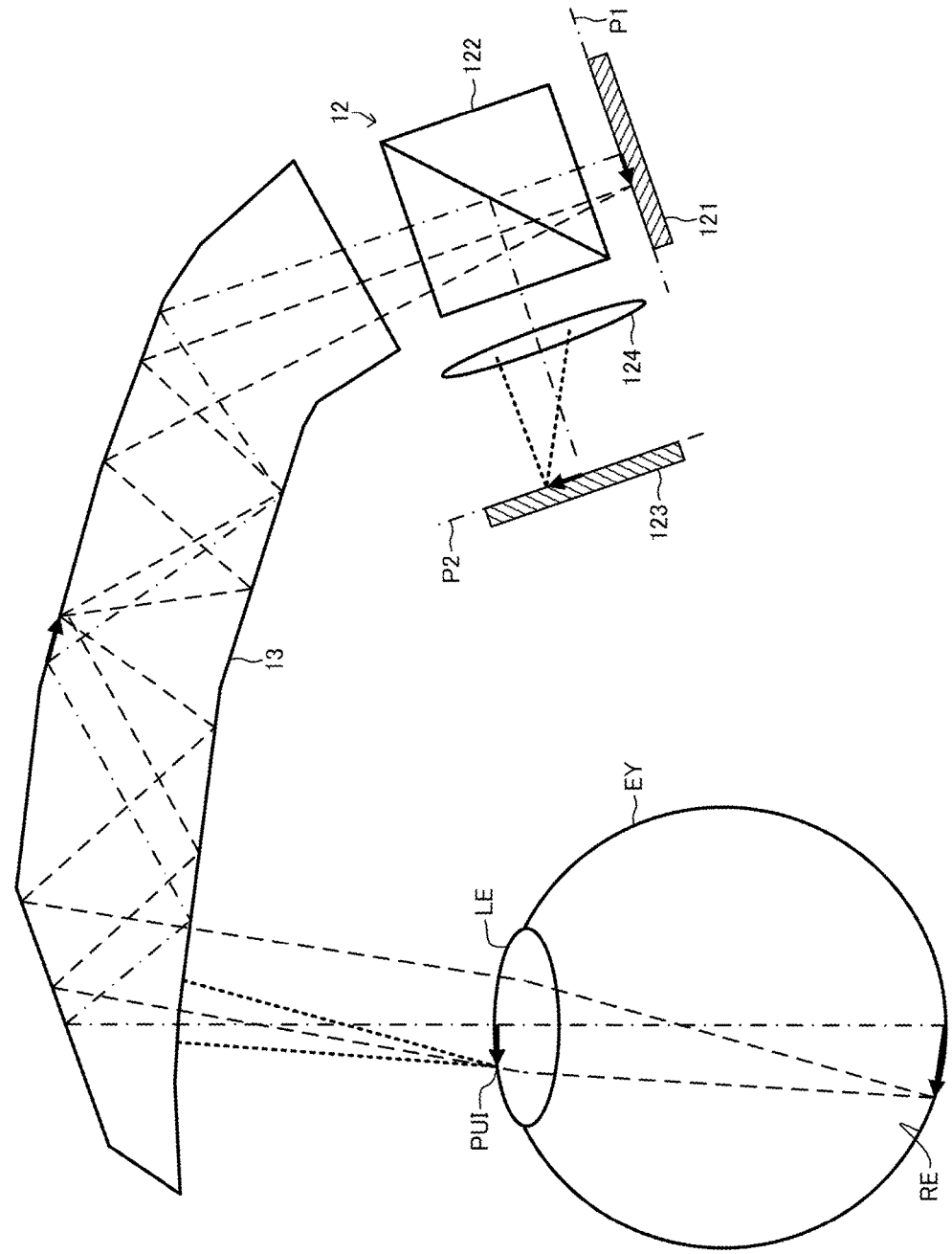
FIG. 6 is a diagram illustrating a configuration of a light source unit and a projecting unit of a first modification to the first embodiment.

As depicted in FIG. 6, in an image display apparatus 1 of the first modification to the first embodiment, the light source unit 12 includes a relay lens 124. The plurality of reflection light rays that have been split by the splitting part 122 enter the relay lens 124. The relay lens 124 guides a plurality of reflection light rays incoming from the splitting part 122 to the detecting part 123. The relay lens 124 focuses reflection light rays from the surface PUI of the pupil and the iris in the eye EY on the second plane P2. The surface PUI of the pupil and the iris may also be referred to as the pupil surface. The pupil surface PUI is one example of a certain site of the eye EY.

In this example, for each of the pixels in the image, the position of the light source on the first plane P1, and the location where the light ray converges on the retina RE are optically conjugate to each other. Further, in this example, for each of the pixels in the image, the position of detector on the second plane P2, and the position in the pupil surface PUI are optically conjugate to each other.

The detecting part 123 detects the intensities of the plurality of reflection light rays incoming from the relay lens 124.

Figure 7:
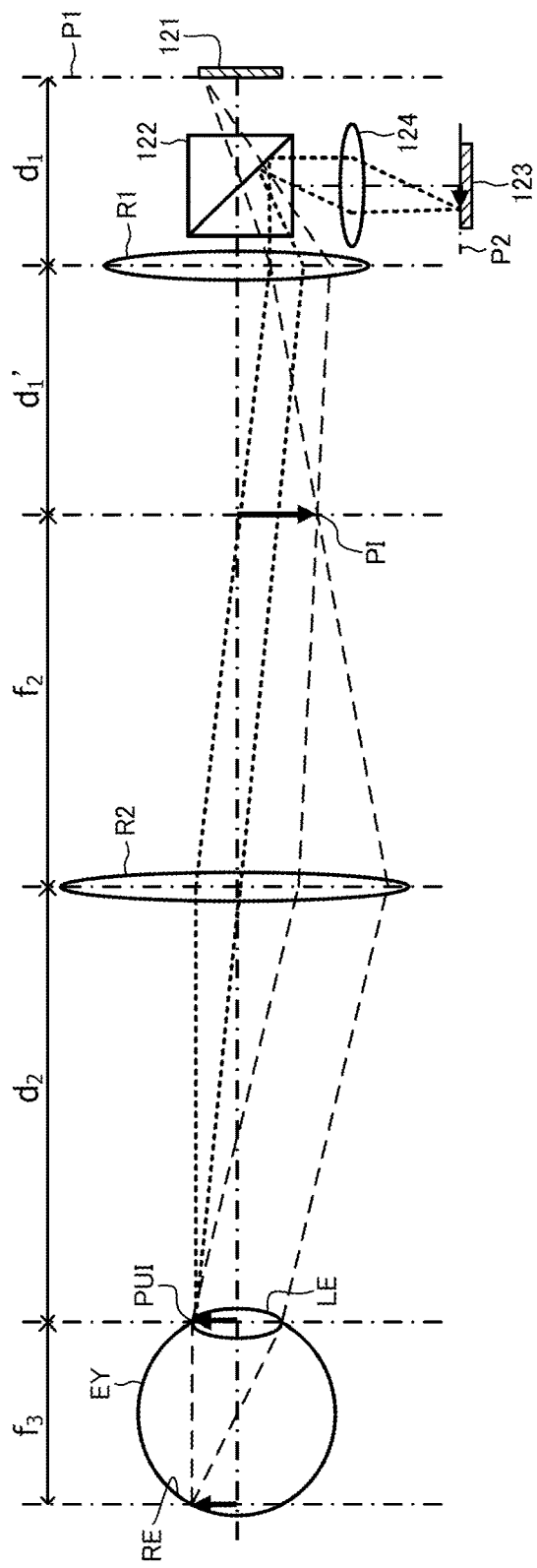
FIG. 7 is a conceptual illustration depicting an optical system employed by the light source unit and the projecting unit in FIG. 6.

FIG. 7 is a conceptual representation of the optical system employed by the light source unit 12 and the projecting unit 13.

In this example, the distance $d_2$ between the principal plane of the second lens R2 and the pupil surface PUI is sufficiently close to the focal length $f_2$ of the second lens R2. Accordingly, the second lens R2 guides a reflection light ray at a point on the pupil surface PUI, as light rays traveling in substantially parallel to each other, to the first lens R1. The first lens R1 and the relay lens 124 converge the light rays that are incoming from the second lens R2 and travel in substantially parallel to each other, on a single point on the second plane P2.

In accordance with the image display apparatus 1 of the first modification to the first embodiment, the condition of the pupil surface PUI can be detected quite precisely without the user being aware that their eye EY is being examined.

In the meantime, diseases, such as diseases of the autonomic nervous system and the optic nerves, can be examined by determining any change of the pupil in response to a change in the intensity of a light ray illuminating the eye EY.

Accordingly, in accordance with the image display apparatus 1 of the first modification to the first embodiment, examination of the above-listed diseases can be made by measuring the time until the pupil starts to change its diameter after the intensity of a light ray illuminating the eye EY is changed.

Second Modification to First Embodiment

An image display apparatus of a second modification to the first embodiment will be described. The image display apparatus of the second modification to the first embodiment has an optical system different from that of the image display apparatus of the first embodiment. Hereafter, the image display apparatus of the second modification to the first embodiment will be described, focusing on the differences from the first embodiment. In the descriptions of the second modification to the first embodiment, reference symbols that are the same as or corresponding to those of the first embodiment will be used.

Figure 8:
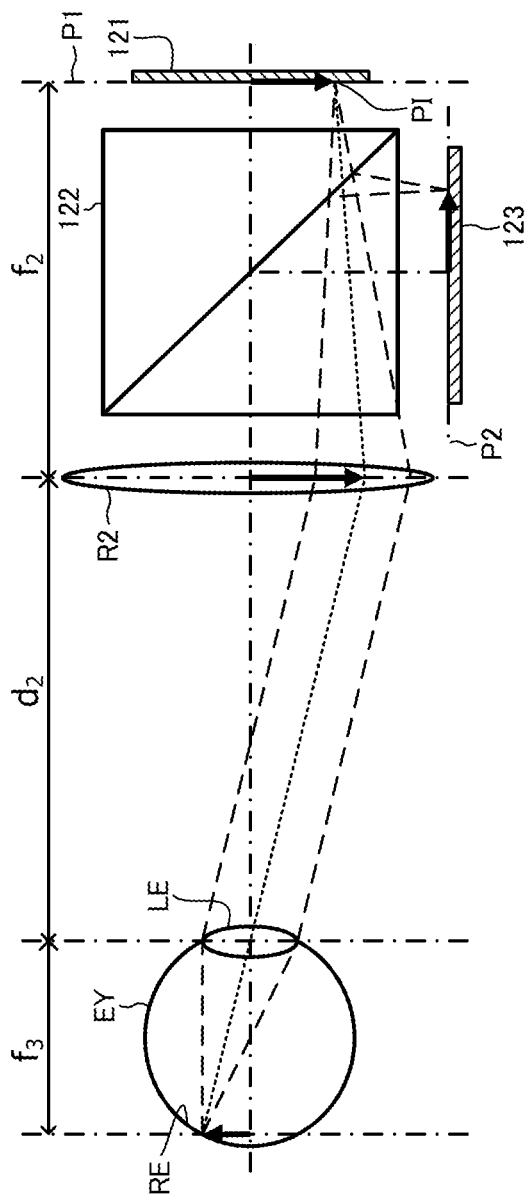
FIG. 8 is a conceptual illustration depicting an optical system employed by the light source unit and the projecting unit of a second modification to the first embodiment.

FIG. 8 is a conceptual representation of the optical system employed by the light source unit 12 and the projecting unit 13 of the second modification to the first embodiment. In this example, the projecting unit 13 functions similarly to the second lens R2.

In this example, the first plane P1 of the light source part 121 may also be referred to as the primary image surface PI.

The second lens R2 is disposed at the position where the distance between the primary image surface PI and the principal plane of the second lens R2 coincides with the focal length $f_2$ of the second lens R2.

The splitting part 122 splits reflection light rays on the optical path between the second lens R2 and the light source part 121. The split reflection light rays for the respective pixels in the image enter the detectors in the detecting part 123.

In accordance with the image display apparatus 1 of the second modification to the first embodiment, advantages and effects similar to those of the image display apparatus 1 of the first embodiment can be achieved.

Third Modification to First Embodiment

An image display apparatus of a third modification to the first embodiment will be described. The image display apparatus of the third modification to the first embodiment has an optical system different from that of the image display apparatus of the first embodiment. Hereafter, the image display apparatus of the third modification to the first embodiment will be described, focusing on the differences from the first embodiment. In the descriptions of the third modification to the first embodiment, reference symbols that are the same as or corresponding to those of the first embodiment will be used.

Figure 9:
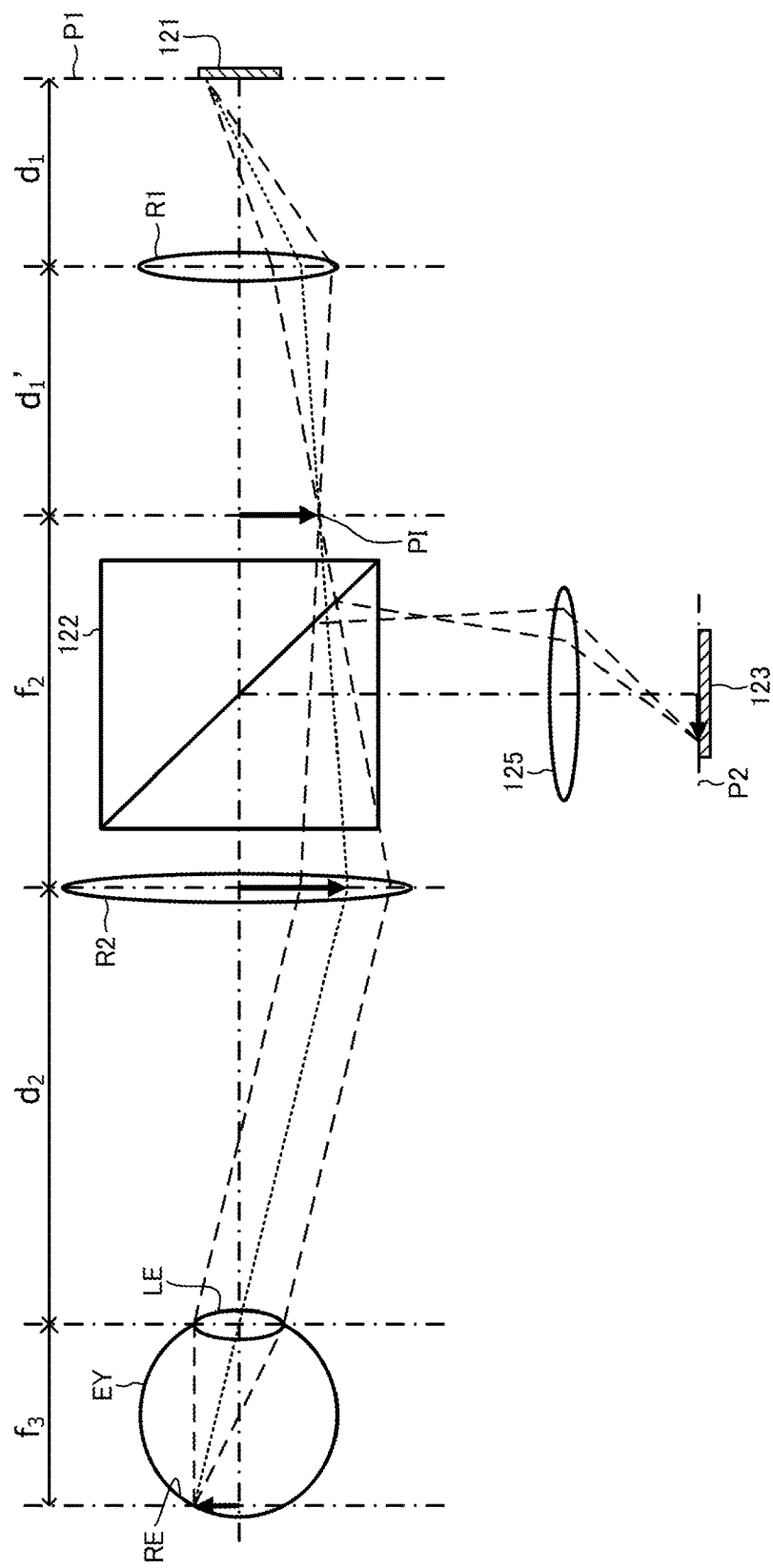
FIG. 9 is a conceptual illustration depicting an optical system employed by the light source unit and the projecting unit of a third modification to the first embodiment.

FIG. 9 is a conceptual representation of the optical system employed by the light source unit 12 and the projecting unit 13 of the third modification to the first embodiment. In this example, the light source unit 12 and the projecting unit 13 are united into a single unit. The light source unit 12 includes a relay lens 125.

In this example, the light source unit 12 and the projecting unit 13 have functions similar to those of the first lens R1, the second lens R2, the splitting part 122, and the relay lens 125.

In this example, the splitting part 122 splits reflection light rays on the optical paths between the second lens R2 and the primary image surface PI.

The plurality of reflection light rays that have been split by the splitting part 122 enter the relay lens 125. The relay lens 125 guides a plurality of reflection light rays incoming from the splitting part 122 to the detecting part 123. The relay lens 125 focuses the reflection light rays from the retina RE on the second plane P2.

The detecting part 123 detects the intensities of the plurality of reflection light rays incoming from the relay lens 125.

In accordance with the image display apparatus 1 of the third modification to the first embodiment, advantages and effects similar to those of the image display apparatus 1 of the first embodiment can be achieved.

Second Embodiment

Next, an image display apparatus of a second embodiment will be described. The image display apparatus of the second embodiment is different from the image display apparatus of the first embodiment in that a scanning projection is employed. Hereafter, the image display apparatus of the second embodiment will be described, focusing on the differences from the first embodiment. In the descriptions of the second embodiment, reference symbols that are the same as or corresponding to those of the first embodiment will be used.

Figure 10:
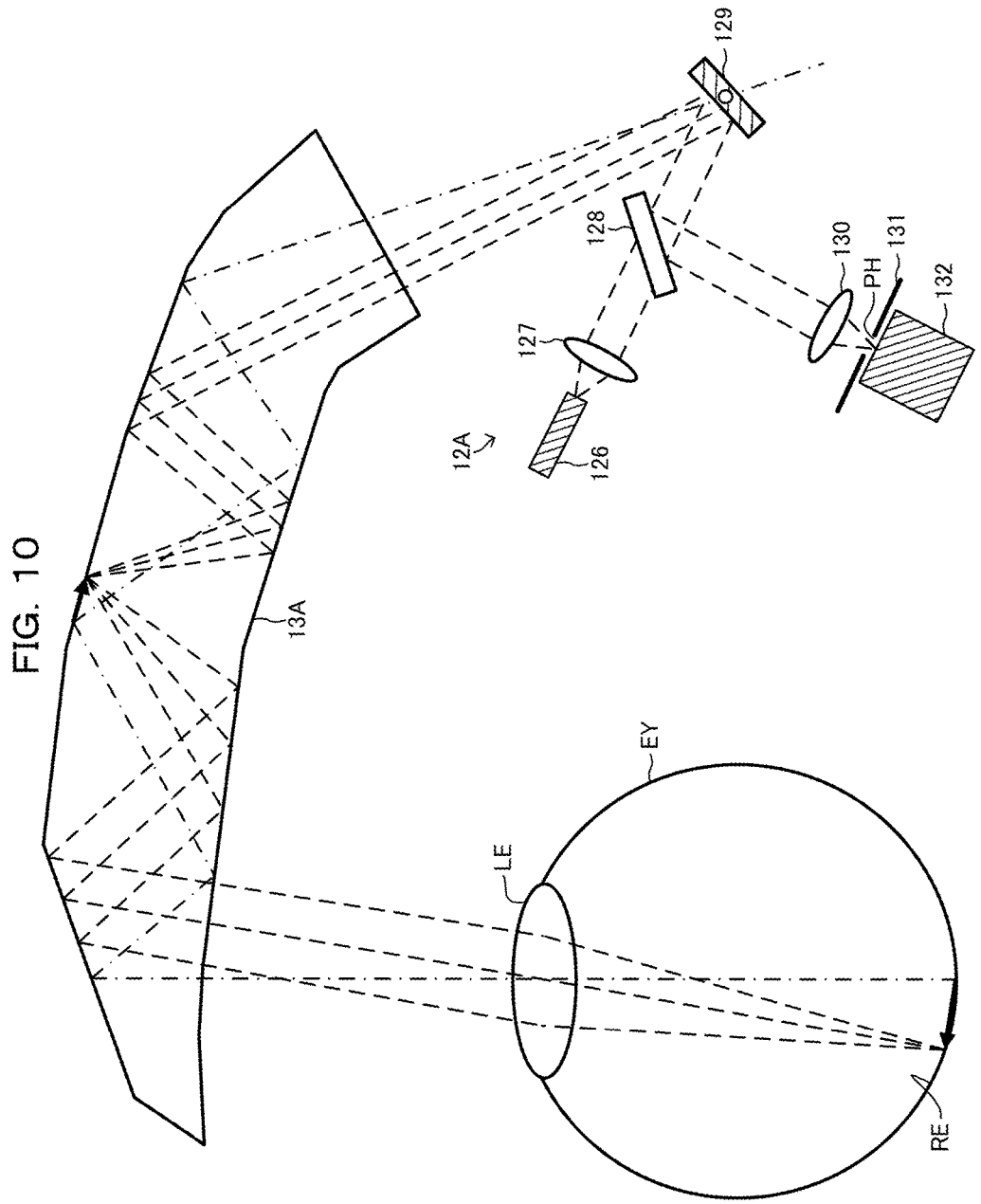
FIG. 10 is a diagram illustrating a configuration of a light source unit and a projecting unit of a second embodiment.

As depicted in FIG. 10, in an image display apparatus 1 of the second embodiment, a main body 10 includes a light source unit 12A and a projecting unit 13A, in place of the light source unit 12 and the projecting unit 13 of the first embodiment.

The light source unit 12A includes a light source part 126, a lens 127, a splitting part 128, a mirror 129, a lens 130, a pinhole filter 131, and a detecting part 132.

The light source part 126 includes a light source that generates a laser light ray. The light source generates one among a plurality of light rays corresponding to respective pixels in the image indicated in the image information received from the controller 20, for every time a predetermined time period elapses.

In this example, the light source generates laser light rays in N colors. N represents the number of colors generated by the light source. In this example, N is three. In this example, the light source generates light rays in red, blue, and green. N may be an integer of 1, 2, or 4 or greater. In other words, the laser light rays generated by the light source include light rays in N colors.

In this example, the light source is a semiconductor laser. The light source may be a laser different from semiconductor lasers.

The plurality of light rays generated by the light source part 126 enter the lens 127. The lens 127 guides a light ray incoming from the light source part 126, as light rays traveling in parallel to each other (in other words, parallel light rays).

The light rays from the lens 127 enter the splitting part 128. The splitting part 128 guides the light rays incoming from the lens 127 to the mirror 129.

The light ray generated by the light source part 126 enters the mirror 129, through the lens 127 and the splitting part 128. The mirror 129 includes a reflective surface, reflects the incoming light ray on the reflective surface, and guides the reflected light ray to the projecting unit 13A. In this example, a light ray that travels from the light source part 126 toward the eye EY, is referred to as a projection light ray.

The mirror 129 controls the normal direction of the reflective surface such that reflected light ray scans at a plurality of positions corresponding to the respective pixels in the image. The scanning is carried out such that the scanned position corresponds to the position of the pixel corresponding to the light ray generated by the light source part 126.

In this example, the mirror 129 is a micro mirror. The micro mirror is one example of a MEMS. The mirror 129 may be a mirror different from micro mirrors.

The projecting unit 13A defines an optical path from the light source part 126 to the eye EY. The light ray generated by the light source part 126 (in other words, projection light ray) enters the projecting unit 13A, through the lens 127, the splitting part 128, and the mirror 129. The projecting unit 13A forms the image on the retina RE by projecting the incoming projection light ray, directly on the retina RE of the eye EY through the defined optical path.

Furthermore, the plurality of light rays reflected at the positions corresponding to the respective pixels in the image to be formed on the retina RE, in a certain site of the eye EY, enter the projecting unit 13A. In this example, a light ray traveling from the eye EY toward the detecting part 132 is referred to as a reflection light ray. In this example, the certain site of the eye EY is the retina RE of the eye EY.

The projection light ray reflected by the mirror 129 are reflected at the position corresponding to the normal direction of the reflective surface of the mirror 129, at the retina RE. The reflected light ray (in other words, reflection light ray) travels on the optical path from the retina RE toward the light source part 126, which is the same as the optical path on which the light ray has traveled to reach the retina RE from the light source part 126. In other words, the reflection light ray travels on the same optical path as that of the projection light ray from which the reflection light ray is originated, but in the direction opposite to the direction of the projection light ray.

The reflection light ray from the projecting unit 13A enters the mirror 129. The mirror 129 reflects the incoming reflection light ray at its reflective surface, and guides the reflected reflection light ray, to the splitting part 128.

The reflection light ray from the mirror 129 enters the splitting part 128. The splitting part 128 splits the incoming reflection light ray from the mirror 129, and guides the split reflection light ray to the lens 130. In this example, the splitting part 128 is a beam splitter.

The reflection light rays split by the splitting part 128 enter the lens 130. The lens 130 converges the light rays that are incoming from the splitting part 128 and travel in parallel to each other, on a single point at the detecting part 132.

The pinhole filter 131 includes a pinhole PH. The pinhole filter 131 is disposed in the vicinity of the detecting part 132 such that the optical path of a reflection light ray from the lens 130 to the detecting part 132 passes through the pinhole PH.

The detecting part 132 includes a detector. The reflection light ray exiting the lens 130 enters the detector. The detector detects the reflection light ray incoming from the lens 130. In this example, the detector detects the intensity of the reflection light ray incoming from the lens 130. In this example, the detecting part 132 is a photodiode including a filter or a spectral element.

Figure 11:
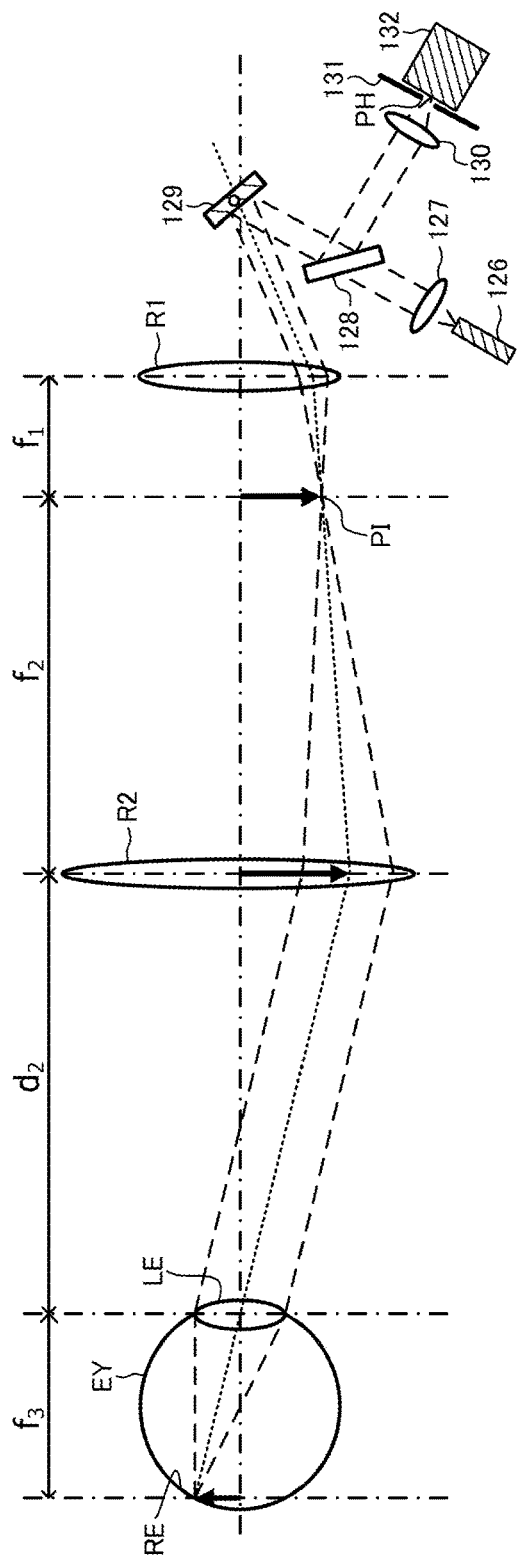
FIG. 11 is a conceptual illustration depicting an optical system employed by the light source unit and the projecting unit in FIG. 10.

The optical system employed by the light source unit 12A and the projecting unit 13A will be described. FIG. 11 is a conceptual representation of the optical system employed by the light source unit 12A and the projecting unit 13A. In this example, the projecting unit 13A functions similarly to the first lens R1 and the second lens R2.

The section from the eye EY to the primary image surface PI, of the optical system employed by the light source unit 12A and the projecting unit 13A of the second embodiment, is the same as the section from the eye EY to the primary image surface PI, of the optical system employed by the light source unit 12 and the projecting unit 13 of the first embodiment.

The first lens R1 is disposed at the position where the distance between the primary image surface PI and the principal plane of the first lens R1 coincides with the focal length $f_1$ of the first lens R1. As a result, the first lens R1 converges parallel light rays incoming from the mirror 129, on a single point on the primary image surface PI. This causes the first lens R1 to form the image on the primary image surface PI.

As set forth above, a projection light ray generated by the light source part 126 are reflected at the position corresponding to the normal direction of the reflective surface of the mirror 129, in the retina RE. The reflection light ray travels on the same optical path as the optical path on which the light ray has traveled to reach the retina RE from the light source part 126, from the retina RE toward the light source part 126.

The splitting part 128 splits the reflection light ray on the optical path between the mirror 129 and the light source part 126. The split reflection light ray enters the detector of the detecting part 132 through the lens 130 and the pinhole PH.

In other words, the position of the light source of the light source part 126 and the position of the detector of the detecting part 132 are optically conjugate to each other. In the meantime, the reflectivity of the retina RE is quite low. Nevertheless, in accordance with the image display apparatus 1, the reflection light ray can be collected to the detector with a high efficiency.

The position of the light source part 126 and the position of the detecting part 132 may be interchangeable.

In this example, the timing S (n, i, j) for generating the light ray of the pixel of the $i^{th}$ row and $j^{th}$ column in $n^{th}$ color, among the light ray colors generated by the light source part 126 is represented by Formula 18. For example, the timing to generate a light ray for each pixel is the timing to initiate generation of the light ray for that pixel:

$$S(n,i,j)=i(\Delta t_0+\Delta t_1)+j(\Delta t_0+\Delta t_0+\Delta t_2)$$  Formula 18 where $\Delta t_0$ represents the time duration during which generation of a light ray for each pixel lasts; $\Delta t_1$ represents the time required to modify the normal direction of the reflective surface of the mirror 129, which corresponds to a movement between two pixels that are adjacent to each other in the X axis direction in the image, and a movement between both of the end pixels in the Y axis direction in the image; and $\Delta t_2$ represents the time required to modify the normal direction of the reflective surface of the mirror 129, which corresponds to a movement between two pixels that are adjacent to each other in the Y axis direction in the image.

In this example, the image display apparatus 1 generates a light ray for each pixel based on the timing S (n, j) represented by Formula 18, and obtains the intensity of the reflection light ray for that pixel.

In this example, the image display apparatus 1 employs the raster scanning. The image display apparatus 1 may use a scanning projection other than the raster scanning.

If the light source generates light rays in N colors one by one, the image display apparatus 1 may use Formula 19 in place of Formula 18:

$$S(n,i,j)=i(\Delta t_0+\Delta t_1)+j(\Delta t_0+\Delta t_2)+(n-1)\{i_0(\Delta t_0+\Delta t_1)+j_0(\Delta t_0+\Delta t_2)\}$$  Formula 19

In accordance with the image display apparatus 1 of the second embodiment, advantages and effects similar to those of the image display apparatus 1 of the first embodiment can be achieved.

In the meantime, the optical system that receives a reflection light ray using the pinhole at the position that is optically conjugate to the position of the light source is an optical system similar to the one used in confocal microscopes (in other words, a confocal optical system).

Therefore, in accordance with the image display apparatus 1 of the second embodiment, any reflected and scattered light components from the vicinity of the point (in other words, focal point) in the retina RE where projection light rays illuminate, included in light rays entering the detector of the detecting part 132, can be reduced by the pinhole filter 131. As a result, the intensity of a reflection light ray from the focal point can be detected quite precisely. Accordingly, the condition of the retina RE can be examined quite precisely, based on the intensity of the detected reflection light ray.

Further, in accordance with the image display apparatus 1 of the second embodiment, reflected light components from positions other than the position that is optically conjugate to the position of the detector of the detecting part 132 (e.g., positions other than the focal point in the retina RE, the boundary surface between optical elements on the optical path, or the like), included in light rays entering the detector of the detecting part 132, can also be reduced by the pinhole filter 131. Since this leads to an improved signal to noise ratio, the intensity of a reflection light ray from the focal point can be detected quite precisely. Accordingly, the condition of the retina RE can be examined quite precisely, based on the intensity of the detected reflection light ray.

The image display apparatus 1 may use an optical fiber, in place of the pinhole filter 131. In this case, the image display apparatus 1 may use an optical path through the optical fiber, in place of the pinhole PH in the pinhole filter 131.

In the meantime, if a light ray generated by the light source part 126 is polarized, the image display apparatus 1 may include an optical isolator for improving the efficiency of utilization of light. For example, such an optical isolator includes a polarized light beam splitter, a wave plate, and a Faraday element. The image display apparatus 1 may also include a transmission-type screen (e.g., micro lens array) that is disposed on the primary image surface PI to control the light distribution.

The image display apparatus 1 may include a plurality of splitting parts disposed at respective positions on the optical path and a plurality of detecting parts corresponding to the respective splitting parts, and may detect intensities of reflection light rays at a plurality of sites of the eye EY with the plurality of detecting parts.

For example, the image display apparatus 1 may be applied to an optical coherence tomography (OCT). Tomograms of the retina RE can be obtained using the OCT. This allows an examination of the conditions of the nerve fiber layers and the blood vessel walls of the retina and the like. This enables obtainment of information that can be employed for diagnoses of glaucoma and age-related macular degeneration.

The present invention is not limited to the embodiments described above. Various changes that can be conceived of by those skilled in the art may be made to the above-described embodiments, in without departing from the spirit of the present invention, for example. Any combinations of the above-described embodiments and modifications to the above-described embodiments may be adopted as another modification of above-described embodiments, in without departing from the spirit of the present invention, for example.

What is claimed is:
1. An image display apparatus comprising:
a light source part that generates a plurality of light rays corresponding to respective pixels in an image that changes over time;
a projecting part that defines an optical path from the light source part to an eye, and forms the image on a retina of the eye by projecting the plurality of generated light rays directly on the retina through the optical path;

a splitting part that splits a plurality of reflection light rays from positions in a certain site of the eye on the optical path, the positions corresponding to the respective pixels;

a detecting part that detects intensities of the plurality of reflection light rays that have been split; and a processing part that obtains parameters indicative of conditions of the site at the positions corresponding to the respective pixels, based on intensities of the generated light rays and the intensities of the plurality of reflection light rays, for the respective pixels.

2. The image display apparatus according to claim 1, wherein the obtainment of the parameter comprises dividing an intensity based on the intensity of the detected reflection light ray, by the intensity of the generated light ray.

3. The image display apparatus according to claim 1, wherein the image changes over time, and the obtainment of the parameter comprises dividing an integral value of an intensity based on the intensity of the detected reflection light ray over a predetermined time duration, by an integral value of the intensity of the generated light ray over the time duration.

4. The image display apparatus according to claim 1, wherein the intensity based on the intensity of the detected reflection light ray is a value obtained by subtracting an ambient light intensity from the intensity of the detected reflection light ray.

5. The image display apparatus according to claim 4, wherein the detecting part detects the ambient light intensity while the light source part generates no light ray.

6. The image display apparatus according to claim 1, wherein the processing part obtains a differential value of the parameter with respect to a position.

7. The image display apparatus according to claim 1, wherein the light source part includes a plurality of light sources arranged in a grid on a first plane, the plurality of light sources generating the plurality of light rays, and the detecting part includes a plurality of detectors arranged in a grid on a second plane, which detect the respective reflection light rays that have been split.

8. A method of processing including:

generating a plurality of light rays corresponding to respective pixels in an image that changes over time, by a light source part;

forming the image on a retina of an eye by projecting the plurality of generated light rays directly on the retina through an optical path from the light source part to the eye;

splitting a plurality of reflection light rays from positions in a certain site of the eye on the optical path, the positions corresponding to the respective pixels;

detecting intensities of the plurality of reflection light rays that have been split; and obtaining parameters indicative of conditions of the site at the positions corresponding to the respective pixels, based on intensities of the generated light rays and the intensities of the plurality of reflection light rays, for the respective pixels.

9. The method of processing according to claim 8, wherein the plurality of light rays are generated respectively, by a plurality of light sources that are arranged in a grid on a first plane;

the reflection light rays that have been split are detected respectively, by a plurality of detectors that are arranged in a grid on a second plane.

10. A processing apparatus adapted to obtain parameters indicative of conditions of a site at positions corresponding to respective pixels in an image that changes over time, based on intensities of a plurality of light rays generated by an image display apparatus and intensities of a plurality of reflection light rays detected by the image display apparatus, for the respective pixels, the image display apparatus comprising:

a light source part that generates the plurality of light rays corresponding to the respective pixels;

a projecting part that defines an optical path from the light source part to an eye, and forms the image on a retina of the eye by projecting the plurality of generated light rays directly on the retina through the optical path;

splitting part that splits the plurality of reflection light rays from positions in the certain site of the eye on the optical path, the positions corresponding to the respective pixels; and detecting part that detects the intensities of the plurality of reflection light rays that have been split.

* * * * *